(12) United States Patent
Dietz et al.

(10) Patent No.: US 9,482,730 B2
(45) Date of Patent: Nov. 1, 2016

(54) MAGNETIC RESONANCE APPARATUS WITH TOUCHSCREEN IN FLEXIBLE FOIL HOUSING

(75) Inventors: Peter Dietz, Fürth (DE); Annette Stein, Erlangen (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 900 days.

(21) Appl. No.: 13/603,499

(22) Filed: Sep. 5, 2012

(65) Prior Publication Data

US 2013/0234712 A1 Sep. 12, 2013

(30) Foreign Application Priority Data

Sep. 9, 2011 (DE) .................. 10 2011 082 411

(51) Int. Cl.
*G01R 33/38* (2006.01)
*G01R 33/28* (2006.01)
*A61B 5/00* (2006.01)

(52) U.S. Cl.
CPC ............. *G01R 33/38* (2013.01); *A61B 5/748* (2013.01); *G01R 33/28* (2013.01)

(58) Field of Classification Search
USPC .......................... 324/300–322; 600/407–435
See application file for complete search history.

(56) References Cited

U.S. PATENT DOCUMENTS

| | | | |
|---|---|---|---|
| 5,345,177 A * | 9/1994 | Sato et al. | 324/318 |
| 6,414,489 B1 * | 7/2002 | Dean et al. | 324/318 |
| 6,437,568 B1 * | 8/2002 | Edelstein et al. | 324/318 |
| 2005/0040825 A1 * | 2/2005 | Sellers et al. | 324/318 |
| 2013/0234709 A1 * | 9/2013 | Hierl et al. | 324/318 |
| 2013/0234711 A1 * | 9/2013 | Dietz et al. | 324/319 |
| 2013/0234712 A1 * | 9/2013 | Dietz et al. | 324/319 |
| 2013/0234713 A1 * | 9/2013 | Maciejewski et al. | 324/321 |
| 2015/0305691 A1 * | 10/2015 | Rothgang | A61B 5/748 600/410 |

FOREIGN PATENT DOCUMENTS

| | | |
|---|---|---|
| CN | 1344928 A | 4/2002 |
| CN | 1409124 A | 4/2003 |
| CN | 18790033 A | 12/2006 |
| CN | 101061390 A | 8/2010 |
| CN | 101796425 A | 8/2010 |
| DE | 1547085 A1 | 10/1969 |
| DE | 102006008724 A1 | 11/2007 |
| DE | 102007037851 A1 | 2/2009 |
| JP | H02218345 A | 8/1990 |

OTHER PUBLICATIONS

SoundCoat Technical Data sheet covering the trademarked Soundfoam-ML HY (2pages) from May 2009 (3) Published by Soundcoat corporation.*

* cited by examiner

*Primary Examiner* — Melissa Koval
*Assistant Examiner* — Tiffany Fetzner

(57) ABSTRACT

A magnetic resonance apparatus is proposed. The magnetic resonance apparatus has a magnet unit and a housing unit. The housing unit has a housing shell unit. The housing shell unit surrounds the magnet unit. The housing shell unit at least partly has a flexible material. Effective noise protection for operation of the magnetic resonance apparatus is provided.

8 Claims, 2 Drawing Sheets

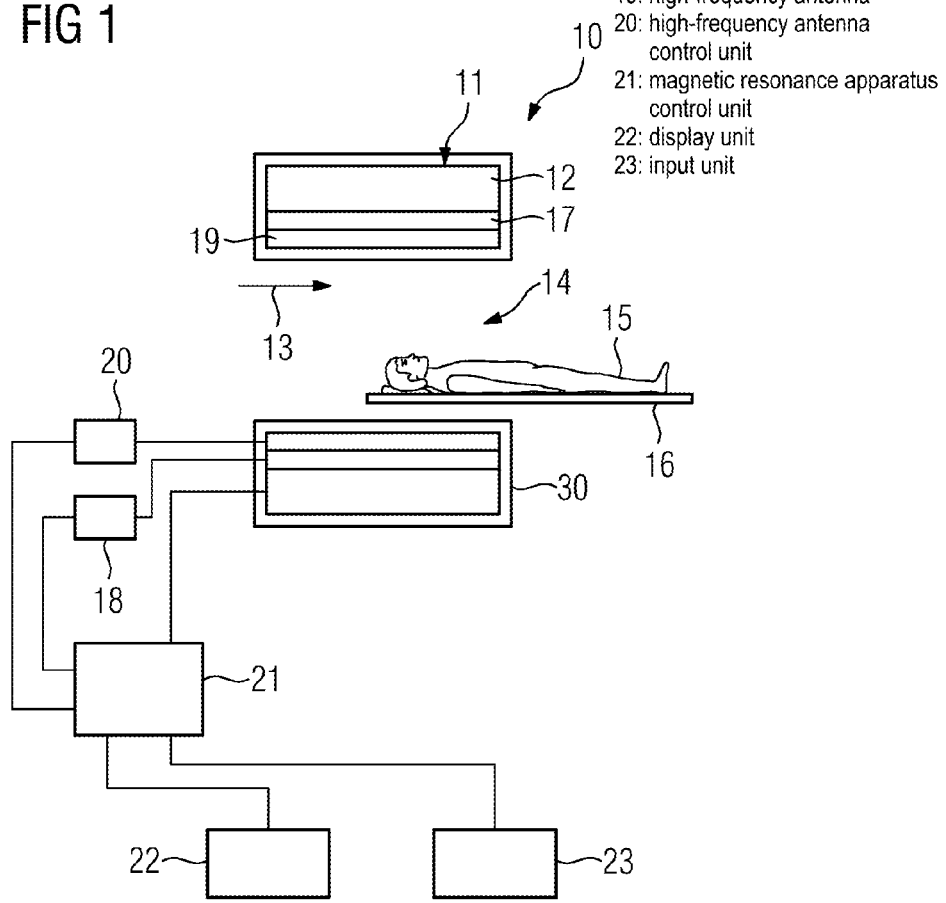

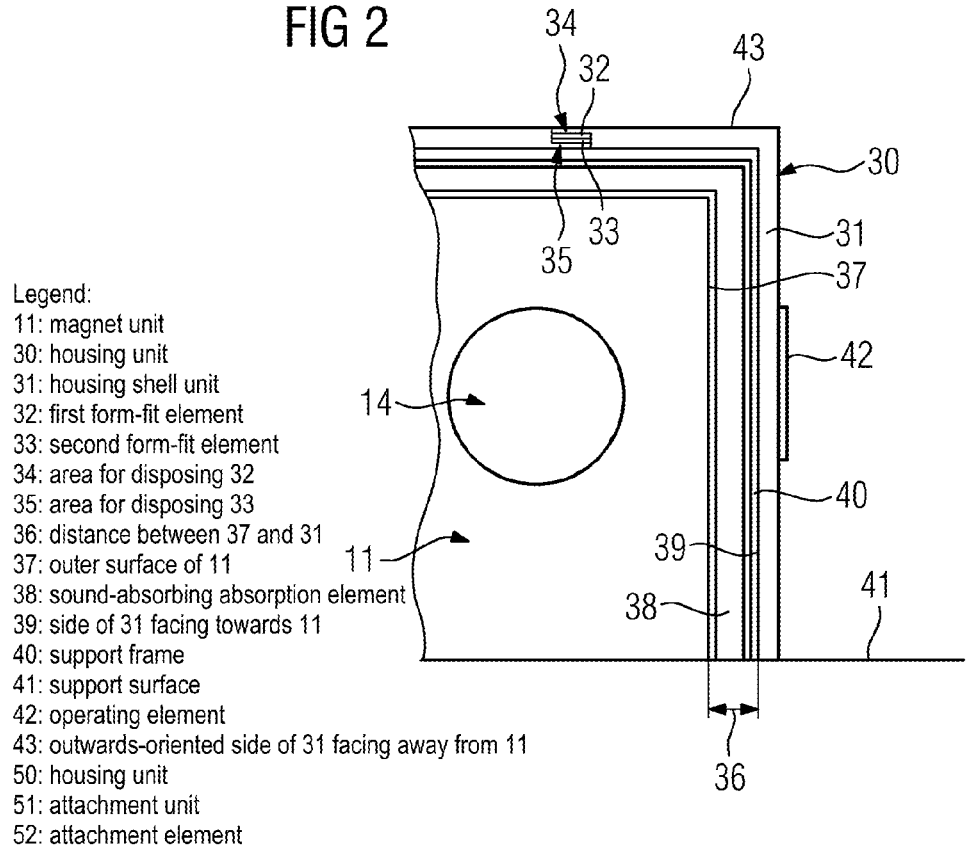
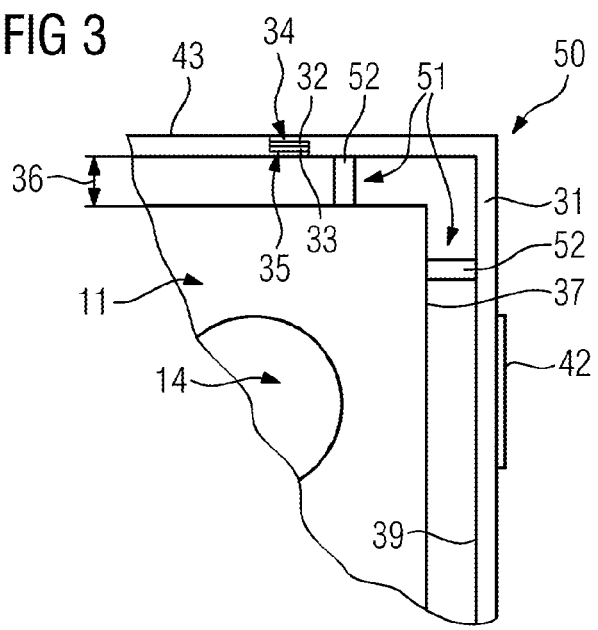

US 9,482,730 B2

MAGNETIC RESONANCE APPARATUS WITH TOUCHSCREEN IN FLEXIBLE FOIL HOUSING

CROSS REFERENCE TO RELATED APPLICATIONS

This application claims priority of German application No. 10 2011 082 411.1 filed Sep. 9, 2011, which is incorporated by reference herein in its entirety.

FIELD OF INVENTION

The present application relates to a magnetic resonance apparatus with a magnet unit and the housing unit with a housing shell unit surrounding the magnet unit.

BACKGROUND OF INVENTION

During operation, magnetic resonance apparatuses generate high levels of noise, which have an unpleasant effect on a patient occupying an imaging area of the magnetic resonance apparatus for an examination. These high levels of operating noise are generated within a magnet unit of the magnetic resonance apparatus. Sound waves are transmitted in such cases from the gradient system of the magnet unit to a main magnet of the magnet unit. From this main magnet the noise is transferred to a housing unit of the magnetic resonance apparatus and from there it is emitted into a space surrounding the magnetic resonance apparatus.

Conventional housing units of magnetic resonance apparatuses have a hard-shell, rigid housing shell unit which is composed of various individual parts. The result is that there can be undesired gaps between the individual parts which make it possible for sound waves of the magnet unit to be transmitted into a space surrounding the magnet unit and the housing unit. In addition hard-shell housing units have good noise emission characteristics.

SUMMARY OF INVENTION

The object of the present application lies in providing effective noise protection for operation of the magnetic resonance apparatus, in which sound wave emission is minimized. The object is achieved by the features of the independent claims. Embodiments are described in the dependent claims.

The application is based on a magnetic resonance apparatus with a magnet unit and a housing unit with housing shell unit surrounding the magnet unit.

It is proposed that the housing shell unit comprises at least a flexible material, through which an effective noise protection for operation of the magnetic resonance apparatus with a minimal sound wave emission can be provided. The housing shell unit is formed completely from the flexible material so that a transmission by the housing shell unit of oscillation energy from oscillation waves disposed in the audible range is reduced and in this way an emission of sound waves to a side of the housing unit facing away from the magnet unit is minimized. In addition local sound influences and or entry of sound into the housing shell unit can be compensated for as a result of the flexible nature of the housing unit, since the transport of sound waves, such as solid-borne sound waves, to a surface of the flexible housing shell unit is prevented. Furthermore, on account of the flexibility of the housing shell unit, a flexible housing shell unit can be achieved, which can for example compensate for tolerances of other components of the magnetic resonance apparatus. In this context a flexible housing shell unit is to be understood as a housing shell unit of which the resonant frequency is disposed above at least 3000 Hz.

It is further proposed that the flexible material has a coincidence frequency of at least 5 kHz. This enables a coupling, such as a transmission and/or transport of sound waves in a range audible to a human being to be suppressed, wherein a plurality of noises that are generated during operation of the magnetic resonance apparatus and audible to the patient are disposed below the frequency of 5 kHz. The flexible material however exhibits a coincidence frequency of at least 8 kHz to 10 kHz. In this context a coincidence frequency is to be understood as a frequency in which a coupling of sound waves from air and of sound waves from the housing shell unit can occur, whereby the frequency of the sound waves of air is equal to the frequency, such as the resonant frequency, of sound waves of the housing shell unit.

In a development of the application it is proposed that the flexible material has a surface density of at least 5 kg/m², such as of 5 kg/m² to 8 kg/m². The flexible housing shell unit with the high surface density acts here as a spring mass unit, in which the housing shell unit, because of its flexible design, causes a decoupling between the two housing shell units during a propagation of sound waves, wherein the flexible housing shell unit additionally has a high mass inertia because of the high density, which supports the decoupling during the propagation of sound waves. An acoustic spring element of a spring mass unit can be formed in this case from an elastic foam which additionally can also be formed from a sound-absorbing absorption element, so that in addition a low height and adaptation to the shape of the magnet unit can be achieved. As an alternative to this the acoustic spring element can also be formed by air.

For an effective sound wave decoupling it is for the housing shell unit to be disposed in a radial direction at a distance from the magnet unit. A distance between the housing shell unit and the magnet unit amounts to at least 2 cm, but to at least 3 cm to 5 cm. A distance between the housing shell unit and the magnet unit is tailored in such cases in respect of noise decoupling and in respect of compactness of the magnetic resonance apparatus, wherein a reduction in the distance by half of the distance results in almost a doubling of a sound pressure.

If the housing unit has at least one sound-absorbing absorption element which is disposed between the magnet unit and the housing shell unit, an additional sound wave decoupling between the housing shell unit and the magnet unit can be achieved here. The sound-absorbing absorption element can for example be formed from a sound-absorbing material such as a foam material and/or a fleece material and/or an amorphous material and/or further materials appearing sensible to the person skilled in the art. In this context a sound-absorbing absorption element is to be understood as an absorption element which is specifically designed to convert sound energy of sound waves into oscillation energy of non-audible oscillation waves and accordingly to reduce or to prevent a reflection of audible sound waves at a boundary surface. In such cases the sound waves, such as airborne sound waves, excite individual particles, such as foam particles for example, of the absorption element into oscillations, wherein the generated oscillation energy is converted within the absorption element into heat energy. In this way oscillation energy is removed from the sound waves, such as the airborne sound waves and the airborne sound waves are damped.

It is further proposed that the housing shell unit has at least a first form-fit element and at least a second form-fit element corresponding to the first form-fit element. In this way the housing shell unit made of the flexible material can be disposed in respect of a transmission of sound waves tightly, such as without any gaps and/or holes, around the magnet unit and in this way an undesired noise bridge and/or sound wave bridge between the magnet unit and a space surrounding the housing shell unit and the magnet unit can be prevented. The at least two form-fit elements are disposed in different areas of the housing shell unit, wherein the two areas are able to be connected to one another without any gaps by the form-fit elements. The first and the second form-fit element can in this case comprise a snap-fit element and/or a friction-fit element and/or further form-fit elements appearing sensible to a person skilled in the art.

In a further embodiment of the application it is proposed that the housing unit has at least one operating element which is integrated on the housing shell unit. In this case the operating element is disposed and/or integrated on a side facing away from the magnet unit so that a compact magnetic resonance apparatus can be provided. The operating element is formed by a touchscreen-type operating element.

A decoupling in respect of a transmission of sound waves between the magnet unit and the housing shell unit can be achieved if the housing unit has a supporting frame embodied separately to the magnet unit on which the housing shell unit is disposed around the magnet unit. The separate supporting frame is disposed so that it is not in contact with the magnet unit and is positioned on a support surface for the magnetic resonance apparatus.

There can further be provision for the housing unit to have at least one attachment unit for attaching the housing shell unit to the magnet unit so that a compact and space-saving magnetic resonance apparatus can be achieved.

BRIEF DESCRIPTION OF THE DRAWINGS

Features and details of the application emerge from the embodiments described below and also with reference to the drawings, in which:

FIG. 1 shows a schematic of a disclosed magnetic resonance apparatus with a housing unit, FIG. 2 shows a first design variant of the housing unit and FIG. 3 shows a second design variant of the housing unit.

DETAILED DESCRIPTION OF INVENTION

FIG. 1 shows a schematic of a disclosed magnetic resonance apparatus. The magnetic resonance apparatus 10 comprises a magnet unit 11 with a main magnet 12 for generating a strong and constant main magnetic field 13. In addition the magnetic resonance apparatus 10 has a cylindrical receiving area 14 for receiving a patient 15, wherein the receiving area 14 is surrounded in a circumferential direction by the magnet unit 11. The patient 15 can be pushed by a patient couch 16 of the magnetic resonance apparatus 10 into the receiving area 14. For this purpose the patient couch 16 is disposed so that it is able to be moved within the magnetic resonance apparatus 10. Furthermore the magnetic resonance apparatus 10 has a housing unit 30 surrounding the magnet unit 11.

The magnet unit 11 also has a gradient coil 17 for generating magnetic field gradients which are used for local encoding during imaging. The gradient coil 17 is controlled by a gradient control unit 18. Furthermore the magnet unit 11 has a high-frequency antenna 19 and a high-frequency antenna unit 20 for exciting a polarization, which is produced in the main magnetic field 13 generated by the main magnet 12. The high-frequency antenna 19 is controlled by the high-frequency unit 20 and emits high-frequency magnetic resonance sequences into an examination area which is formed by the receiving area 14. This deflects the magnetization from its position of equilibrium. In addition magnetic resonance signals are received by the high-frequency antenna unit 20.

For control of the main magnet 12, the gradient control unit 18 and for control of the high-frequency antenna unit 20 the magnetic resonance apparatus 10 has a control unit 21 formed by a processing unit. The processing unit controls the magnetic resonance apparatus 10 centrally, by controlling processes such as carrying out a predetermined imaging gradient echo sequence. Control information such as imaging parameters, as well as reconstructed magnetic resonance images, can be displayed for an operator on a display unit 22, or or on at least one monitor, of the magnetic resonance apparatus 10. In addition the magnetic resonance apparatus 10 has an input unit 23, by which information and/or parameters can be input by an operator during a measurement process.

The magnetic resonance apparatus 10 shown can of course include further components that magnetic resonance apparatuses 10 usually feature. The way in which a magnetic resonance apparatus 10 generally functions is also known to the person skilled in the art, so that no detailed description of the general components will be provided.

FIG. 2 shows the housing unit 30 of the magnetic resonance apparatus 10 in greater detail. The housing unit 30 has a housing shell unit 31 which is formed from a flexible material, wherein the flexible material has a high surface density. The surface density of the flexible material amounts here to at least 5 kg/m$^2$ to 8 kg/m$^2$. The surface density of the flexible material of the housing shell unit 31 in such cases influences a behavior and/or a property of the housing shell unit 31 for sound wave damping and/or sound wave decoupling of the housing shell unit 31, wherein a large surface density of the flexible material results in a high sound wave damping and/or sound wave decoupling of the housing shell unit 31. However the surface density of the flexible material of the housing shell unit 31 is tailored in respect of an overall weight of the magnetic resonance apparatus 10.

The flexible material in this case can comprise a material with a rubber-like structure. In addition the flexible material can have additional mass particles mixed into it to increase its mass and thereby to raise the surface density. The housing shell unit 31 is also embodied to be compatible with magnetic resonance.

The flexible material of the housing shell unit 31 also has a coincidence frequency of at least 5 kHz, wherein the coincidence frequency represents a frequency, in which a sound wave coupling occurs between the housing shell unit 31 and an area adjoining the housing shell unit 31, which is disposed between the magnet unit 11 and the housing shell unit 31. However the coincidence frequency of the flexible material of the housing shell unit 31, is disposed between 8 kHz and 10 kHz, so that, for the undesired operational noises of the magnet unit 11 during operation of the magnetic resonance apparatus 10, there is a noise decoupling between the magnet unit 11 and the housing shell unit 31.

The housing shell unit 31 also forms a closed cover around the magnet unit 11, so that the housing shell unit 31 is disposed without any gaps and/or holes around the magnet unit 11 and no sound bridges are present to transmit sound waves between the magnet unit 11 and a space surrounding the housing shell unit 31 together with the magnet unit 11. For this purpose the housing shell unit 31 is embodied as a flexible foil with a foil thickness of approximately 5 mm to 7 mm.

In addition the housing shell unit 31 has a least one first form-fit element 32 and at least one second form-fit element 33, wherein the second form-fit element 33 is embodied to correspond to the first form-fit element 32. The form-fit elements 32, 33 are disposed on different areas 34, 35, such as on different edge areas, of the housing shell unit 31. The different edge areas with the form-fit elements 32, 33 disposed thereon are formed by opposing edge areas, so that for an arrangement of the flexible foil of the housing shell unit 31 around the magnet unit 11, these edge areas abut each other or overlap each other for a seamless coverage of the magnet unit 11 by the flexible foil. Because of the form-fit elements 32, 33 at these edge areas these edge areas can be attached and/or linked to each other in a constructively simple manner, so that the housing shell unit 31 also has no free edges which can promote a sound wave emission.

The form-fit elements 32, 33 are typically formed by friction-fit elements and/or by snap-fit elements and/or by further form-fit elements 32, 33 appearing sensible to the person skilled in the art.

In addition it is also conceivable for the magnet unit 11 also to have at least one form-fit element, which corresponds to at least one of the form-fit elements 32, 33 of the housing shell unit 31. In this way it is conceivable to attach the housing shell unit 31 at least partly around the magnet unit 11 or to attach the housing shell unit 31 in areas requiring a space-saving arrangement of the housing shell unit 31 on the magnet unit 11, such as in the area of a patient opening of the receiving area 14 for example.

The housing shell unit 31 is disposed spaced around the magnet unit 11, wherein a distance 36 between an outer surface 37 of the magnet unit 11 and the housing shell unit 31 is at least 2 cm and is disposed between 3 cm and 5 cm.

In addition the housing unit 30 has a sound-absorbing absorption element 38 which is disposed between the magnet unit 11 and the housing shell unit 31. The sound-absorbing absorption element 38 can typically be formed from a foam and/or a fleece and/or an amorphous material and/or further materials appearing sensible to the person skilled in the art. Sound wave decoupling through the housing unit 30 is increased by the sound-absorbing absorption element 38. Reflections of sound at the side 39 of the housing shell element 31 facing towards the magnet unit 11 are reduced by the sound-absorbing material and in this way a formation of standing waves and/or interference manifestations of sound waves between the magnet unit 11 and the housing shell unit 31 are suppressed.

An effective noise reduction lies in a frequency range of approximately 200 Hz at approximately 10 dB through to approximately 15 dB and a wideband range of approximately 20 dB through to approximately 30 dB.

For attaching the housing shell unit 31 the housing unit 30 has a support frame 40 embodied separately to the magnet unit 11 on which the housing shell unit 31 is disposed around the magnet unit 11. The separate support frame 40 is disposed on a support surface 41 for supporting the magnetic resonance apparatus 10 and is disposed as a grid or net around the magnet unit 11 without making contact with the latter so that an undesired coupling-in of sound waves by the support frame 40 onto the housing shell unit 31 is prevented.

The housing unit 30 also has an operating element 42 which is formed by a touchscreen. This operating element 42 is integrated into the housing shell element 31, wherein the operating element 42 is integrated into an outwards-oriented side 43 of the housing shell unit 31 facing away from the magnet unit 11. Supply lines such as power lines and/or data lines which lead to the operating element 42, are integrated within the flexible foil of the housing shell unit 31, wherein the arrangement of the supply lines means that a damping characteristic and or a decoupling characteristic of the housing shell unit 31 in respect of sound waves remains uninfluenced.

FIG. 3 shows an alternative embodiment of the housing unit 50. Components, features and functions which remain the same are basically labeled with the same reference characters. The subsequent description is limited to how this embodiment differs from the embodiment in FIG. 2, wherein in relation to components, features and functions which remain the same, reference is made to the description of the embodiment in FIG. 2.

The housing unit 50 in FIG. 3 has a housing shell unit 31, of which the position relative to the magnet unit 11 of the magnetic resonance apparatus 10 and its embodiment is similar to that given in the description in FIG. 2.

The housing unit 50 has an attachment unit 51 for attaching the housing shell unit 31 to the magnet unit 11. The attachment unit 51 can comprise bar-type attachment elements 52, which extend away in a radial direction from the magnet unit 11 and to the end of which facing away from the magnet unit 11 the housing shell unit 31 is disposed. For an effective sound-wave decoupling between the magnet unit 11 and the housing shell unit 31, the attachment element 52 can also be formed at least partly by a decoupling element and/or a damping element, such as for decoupling and/or damping of sound waves.

The invention claimed is:

1. A magnetic resonance apparatus, comprising:
a magnet unit; and
a housing unit comprising a housing shell unit surrounding the magnet unit, wherein the housing shell unit is embodied as a flexible foil with a foil thickness of approximately 5 mm to 7 mm, and at least one touchscreen operating element integrated into an outward-oriented surface of the housing shell unit that faces away from the magnet unit,
wherein the housing shell unit comprises at least one first form-fit element disposed on at least one internal outer edge area of the housing shell unit,
wherein the housing shell unit further comprises at least one second form-fit element corresponding to the at least one first form-fit element disposed on a corresponding internal interior edge area of the housing shell unit, and
wherein the at least one first form-fit element fits into the corresponding at least one second form-fit element of the housing shell unit so that the edge areas of the housing shell unit containing the at least one first form-fit element and the at least one second form-fit element abut and/or overlap one another whereby the housing shell unit seamlessly surrounds the magnet unit without contacting the magnet unit.

2. The magnetic resonance apparatus as claimed in claim 1, wherein the flexible foil material comprises a coincidence frequency of at least 5 kHz.

3. The magnetic resonance apparatus as claimed in claim 1, wherein the flexible foil material comprises a surface density of at least 5 kg/m2.

4. The magnetic resonance apparatus as claimed in claim 1, wherein the housing shell unit is positioned at a distance of at least 2 cm from the magnet unit.

5. The magnetic resonance apparatus as claimed in claim 1, wherein the housing shell unit comprises at least one sound-absorbing absorption element which is disposed between the magnet unit and the housing shell unit.

6. The magnetic resonance apparatus as claimed in claim 1, wherein the housing unit comprises a support frame which provides structure to the housing shell unit, the support frame being arranged around and spaced apart from the magnet unit, without contacting the magnet unit.

7. The magnetic resonance apparatus as claimed in claim 1, wherein the housing unit comprises at least one bar-type attachment unit configured for attaching an inner surface the housing shell unit to an outer surface of the magnet unit.

8. The magnetic resonance apparatus as claimed in claim 1, wherein the at least one first form-fit element and the at least one second form-fit element comprise either a snap-fit element or a friction-fit element.

* * * * *